United States Patent [19]

Correia et al.

[11] Patent Number: 5,116,799
[45] Date of Patent: May 26, 1992

[54] OXYCHLORINATION OF HYDROCARBONS

[75] Inventors: Yves Correia, Chateau-Arnoux; Jean Lesparre, Volonne; Alain Petit, Martigues, all of France

[73] Assignee: Atochem, Puteaux, France

[21] Appl. No.: 669,864

[22] Filed: Mar. 15, 1991

Related U.S. Application Data

[62] Division of Ser. No. 454,528, Dec. 21, 1989, Pat. No. 5,053,567.

[30] Foreign Application Priority Data

Dec. 26, 1988 [FR] France ................. 88 17181

[51] Int. Cl.⁵ ............... B01J 23/72; B01J 21/08; B01J 21/04
[52] U.S. Cl. ................ 502/225; 502/244; 502/345
[58] Field of Search ........... 502/225, 244, 346, 345; 570/243

[56] References Cited

U.S. PATENT DOCUMENTS

| | | | |
|---|---|---|---|
| 3,420,901 | 1/1969 | Schulz | 502/346 X |
| 3,720,723 | 3/1973 | Prichett | 502/225 X |
| 3,888,791 | 6/1975 | Daumas | 502/242 |
| 4,046,821 | 9/1977 | Croce et al. | 570/243 X |
| 4,339,620 | 7/1982 | Cowfer et al. | 570/243 |
| 4,377,491 | 3/1983 | Canavesi et al. | 502/225 |
| 4,587,230 | 5/1986 | Cavaterra et al. | 502/225 |
| 4,740,644 | 4/1988 | Eichhorn et al. | 502/225 X |

FOREIGN PATENT DOCUMENTS

| | | | |
|---|---|---|---|
| 0713613 | 7/1965 | Canada | 570/243 |
| 0991623 | 6/1976 | Canada | 570/243 |
| 1024998 | 1/1978 | Canada | 502/346 |
| 1027280 | 4/1966 | United Kingdom | 570/243 |
| 1063175 | 3/1967 | United Kingdom | 502/225 |
| 1326428 | 8/1973 | United Kingdom | 570/243 |

*Primary Examiner*—W. J. Shine
*Assistant Examiner*—Douglas J. McGinty
*Attorney, Agent, or Firm*—Burns, Doane, Swecker & Mathis

[57] ABSTRACT

Chlorinated hydrocarbons, e.g., 1,2-dichloroethane, are prepared by heterogeneously oxychlorinating a hydrocarbon with an oxygen-containing gas and gaseous hydrochloric acid in a fluidized bed containing admixture of (i) a catalytically effective amount of an oxychlorination catalyst, (ii) diluent particles of at least one catalytically and chemically inert solid material, and (iii) copper powder or a powdered copper compound.

2 Claims, No Drawings

OXYCHLORINATION OF HYDROCARBONS

This application is a divisional of application Ser. No. 07/454,528, filed Dec. 21, 1989, U.S. Pat. No. 5,053,

BACKGROUND OF THE INVENTION

1. Field of the Invention

The present invention relates to a novel heterogeneous catalytic oxychlorination process for the preparation of chlorinated hydrocarbons, in particular for the production of 1,2-dichloroethane.

2. Description of the Prior Art 1,2-Dichloroethane (D 12) is a compound manufactured industrially on a scale of several million tons per year. Upon pyrolysis thereof, D 12 is converted into vinyl chloride monomer (VCM) and hydrochloric acid (HCl). The VCM is polymerized to poly(vinyl chloride) (or PVC) which is a widely used plastic material. The HCl produced in the pyrolysis is separated from the VCM and then contacted with ethylene and oxygen in the presence of a catalyst to prepare D 12; this constitutes the oxychlorination reaction.

The oxychlorination reaction is very general and can be carried out using most hydrocarbons. Catalytic oxychlorination has been described in numerous patents, in particular in FR 2,063,365, FR 2,260,551, FR 2,213,259 and FR 2,125,748. The catalyst is a copper salt deposited onto powdered alumina.

European Patent Application EP 58,644 describes the preparation of such a catalyst, by pouring a solution of cupric chloride into a fluidized bed of powdered alumina at a maximum temperature of 50° C. This operation is followed by fluid-bed drying in hot air at a temperature not exceeding 140° C.

European Patent Application EP 29,143 describes the preparation of an oxychlorination catalyst, comprising mixing previously prepared catalyst, namely, alumina powder containing a copper compound, with a naked support, namely, alumina powder which does not contain any copper compound, in a fluidized bed during the oxychlorination reaction. The addition of a naked support to a fluid bed, originally charged with catalyst, during the oxychlorination reaction is also described.

This technique is stated to have the advantage of avoiding sticking (or agglomeration) of the catalyst grains during operation. The '143 application also describes a migration of the copper compound from the alumina containing the copper to the naked support. It is thus apparent that the result of this method is a reduction in the copper content of the catalyst, since the amount of support is increased without adding copper. Accordingly, the "suppression or reduction of sticking" is associated not only with the reduction in the amount of copper, but also with the migration of a copper compound from the alumina containing same to the naked support.

EP 29,143 also describes a technique for preparing a catalyst, in situ, by charging the reactor with naked support, fluidizing it with the reaction gas and adding solid cupric chloride thereto. This technique is presented as a substitute for the conventional preparation of the catalyst by impregnation external of the reactor. However, this preparation is suggested only on a laboratory scale, and such preparative technique indeed is not industrial, since, at the start of such preparation, the fluidized bed does not contain any actual catalyst, i.e., a copper compound deposited onto a support. Therefore, no oxychlorination reaction is carried out and it is necessary to initiate a heating stage. But if heating is carried out in the absence of catalyst, an explosive zone exists at the outlet of the fluid bed, because there is no reaction and therefore no conversion.

European Patent EP 119,933 also describes an oxychlorination catalyst based on the same principle as above, i.e., copper impregnating an alumina powder, but without presenting the disadvantage of agglomeration, because there is less copper on the surface than in the interior of the catalyst particles.

The above prior art all relates to fluid oxychlorination beds comprising a "homogeneous" catalyst, namely, all of the grains of which are impregnated with copper values.

Fluid oxychlorination beds including a "heterogeneous" catalyst, i.e., powders of a mixture of alumina particles impregnated with copper values as above and inert particles such as silica sand, have also been employed in this art. These catalysts are described in French Patent 2,242,143. Such "heterogeneous" catalysts do not present the disadvantage of agglomeration or sticking of the "homogeneous" catalysts but, on the other hand, they have the drawback of forming an autoabrasive mixture, the grams of sand effecting wear and attrition of the alumina grains. The copper-rich fines are eliminated and this must be compensated for by additions of fresh catalyst.

SUMMARY OF THE INVENTION

Accordingly, a major object of the present invention is the provision of an improved "heterogeneous" catalytic process for the oxychlorination of hydrocarbons, and wherein the catalytic performance thereof is maintained constant over time.

To avoid confusion with the usual terms in the fields of homogeneous catalysis and heterogeneous catalysis, and to remain consistent with the terms employed in FR 2,242,143, the "heterogeneous" oxychlorination catalysts will herein be designated the "fluidizable charge" or "fluidizable catalytic charge."

Briefly, the present invention features a process for the oxychlorination of a hydrocarbon to form a chlorinated hydrocarbon, in which the hydrocarbon, an oxygen-containing gas and gaseous hydrochloric acid are transferred through a fluidizable charge comprising a mixture of an oxychlorination catalyst and particles of at least one catalytically and chemically inert solid material, and further wherein copper or a copper compound in powder form is added to the fluidized charge.

The present invention also features such catalyst compositions, per se.

Thus, this invention also features a composition useful as an oxychlorination catalyst, comprising a mixture of (i) an oxychlorination catalyst and particles of at least one catalytically and chemically inert solid material, and (ii) powdered copper or a powdered copper compound.

DETAILED DESCRIPTION OF THE PREFERRED EMBODIMENTS OF THE INVENTION

More particularly according to the present invention, the hydrocarbon to be oxychlorinated can be used alone or can be a mixture of several hydrocarbons selected from among aliphatic hydrocarbons having from 1 to 12 carbon atoms, cycloaliphatic hydrocarbons having up to 12 carbon atoms and aromatic hydrocarbons having up to 4 fused benzene nuclei, as well as the chlorinated derivatives thereof. Exemplary such hydrocarbons include methane, ethane, propane, ethylene and propylene. This invention is particularly applicable to ethylene. The oxygen-containing gas is preferably air, but air depleted of or enriched in oxygen can also be used.

The oxychlorination catalysts according to the invention can be any oxychlorination catalyst which can be used, as such, without mixing with a catalytically and chemically inert material. Advantageously, powders are used which are essentially based on alumina and have a particle size ranging from 20 to 200 and a surface area ranging from 90 to 450 $m^2/g$ and preferably from 30 to 90 $\mu$ and from 250 to 400 $m^2/g$. These powders are impregnated with copper or a copper salt in an amount of up to 10% and preferably from 3% to 10% by weight of copper relative to the final product catalyst.

Exemplary catalytically and chemically inert materials serving as a diluent (but in no event as a catalyst support) include microbeads of glass or silica, $\alpha$-alumina and preferably silica sand, which is found in its natural state and the particle size distribution of which is adapted to the requirements of the fluidization.

The particle size distribution of the actual catalyst, on the one hand, and that of the catalytically and chemically inert material on the other are selected such that the diameter and the distribution of particle sizes in the mixture are favorable to ensure good fluidization.

Advantageously, the size of the inert particles ranges from 20 to 200 $\mu$.

The amount of inert material can vary over wide limits. Advantageously, the amount of inerts present ranges from 1 to 20 times the weight of the amount of catalyst.

A primary object of oxychlorination is essentially to use hydrochloric acid as the source of chlorine. The amounts of oxygen and hydrocarbon are thus adjusted to provide a chlorinated hydrocarbon approximately stoichiometrically by consuming the maximum of HCl and hydrocarbon.

Over the course of operation of a typical fluidized bed for oxychlorination, a decrease in catalytic activity is determined, manifested in a lack of hydrocarbon conversion.

This decrease is due to catalyst wear and attrition. In addition to such wear, which entails a decrease in activity, there is a physical loss by entrainment of catalyst fines in the gases at the outlet of the fluid bed. This also results in a less than perfect efficiency of the means for separating the entrained catalyst and the gases. This separation is made difficult by the transformation of a fraction of the catalyst into dust (fines) as a result of attrition. Generally, the reduction in the amount of catalyst and the decrease in its activity are compensated for by additions of fresh catalyst. It has now surprisingly and unexpectedly been found that this decrease in activity can be compensated for by adding powdered copper or a powdered copper compound to the fluidized bed. Exemplary such copper compounds include copper chloride or oxychloride. It is preferred to use elemental copper.

The particle size of the copper compound can vary over wide limits, provided that the compound is fluidizable in the reactor without being too fine, such that it is not entrained at the outlet from the bed. Advantageously, the powder has a particle size ranging from 20 to 500 $\mu$. The powder can be added continuously or discontinuously to the bed. The amount of powder to be introduced is a function of the desired performance.

Advantageously, from 1 to 2 kg (expressed as copper) of powder are introduced per $m^3$ of fluidized bed in operation. The operation can be repeated as often as necessary. It is also possible to add fresh catalysts in addition to the copper compound as a powder.

The copper or copper compound can be in the form of a very copper-rich catalyst. By "very copper-rich" is intended that the content, expressed as a percentage by weight of copper in the finished catalyst, is greater than that of the catalyst in operation in the fluidized charge. Advantageously, this value is 1.2 times, and preferably from 1.5 to 3 times, that of the catalyst in operation in the fluidized charge.

For example, if the catalyst in operation in the fluidized charge contains from 3.5% to 7% by weight of copper, the catalyst additions are made to an extent of about 12% by weight of copper. It is considered that this amount of 12%, expressed as copper values, is very copper-rich. Moreover, this is an unusual value since the procedure for obtaining it is much more complicated than that for the usual values of 3% to 8%.

It is also within the ambit of this invention to add a mixture of at least two materials selected from among copper, a copper compound and a very copper-rich catalyst.

The invention also features the catalytic compositions or fluidizable charges, per se, used in the process immediately above described.

Significant advantages of the present invention relative to the prior art operation (which entails compensating for the decrease in activity and the reduction in catalyst quantity only by additions of fresh catalyst) include a more regular operation, avoidance of disruptions in activity and such improvements are longer-lasting. The copper avoids the sudden variations in activity which would disturb the operation of the process.

In order to further illustrate the present invention and the advantages thereof, the following specific examples are given, it being understood that same are intended only as illustrative and in nowise limitative.

EXAMPLE 1

Test in a lass reactor. 24 mm in diameter and 1 meter in bed height

1. Test No. 1 (not according to the invention):

A catalyst was prepared by impregnating an alumina, the principal phase of which was chi and which contained less than 10% by weight of eta alumina (i.e., a BAYER flash alumina), with $CUCl_2$ to 4% by weight of Cu. The surface area was 384 $m^2/g$, the mean diameter was 53 $\mu$, the pore volume was 36 $cm^3/100$ g and the tap density was 1,000 $kg/m^3$.

79.2 g of catalyst were used.

This catalyst was diluted with silica having a mean diameter of 67 $\mu$ (ranging from 40 to 150 $\mu$) and a tap density of 1,570 $kg/m^3$.

2. Test No. 2 (according to the invention):

The procedure was as in Test No. 1, but 6.4 g of copper powder (300 $cm^2/g$) having a mean diameter of 50 $\mu m$ were added.

3. Test No. 3 (not according to the invention):

An alumina support (170 g) identical to that of Test No. 1, but not impregnated, was mixed with copper powder (76 g). A catalyst was obtained with difficulty (after 34.5 hours), but it was unsuitable for use in the oxychlorination of ethylene to D 12 because of excessive $CO+CO_2$.

4. Test No. 4 (according to the invention):

The procedure was as in Test No. 1, but with addition of alumina impregnated with 5.6 g of copper oxychloride in place of copper.

The results using the catalysts of Tests 1 to 4 for the oxychlorination of ethylene are reported in Table I:

TABLE I

| TEST | 1 | 2 | 3 | 4 |
|---|---|---|---|---|
| Diluent (silica) | 184.9 g | 184.9 g | 0 | 184.9 g |
| HCl/C$_2$H$_4$ (molar ratio) | 1.93 | 1.90 | 1.90 | 1.86 |
| O$_2$/C$_2$H$_4$ (molar ratio) | 0.73 | 0.80 | 0.73 | 0.78 |
| Temperature (°C.) | 230 | 230 | 240 | 230 |
| Conversion rate of C$_2$H$_4$ (%) | 86.9 | After 12.5 hours of operation 93.5 | After 34.5 hours of operation 99.6 | After 17.5 hours of operation 95.3 |
| Conversion rate of HCl (%) | 87.9 | 95.7 | 96.8 | 98.2 |
| Conversion rate to pure D12 (%) | 83.0 | 90.0 | 89.1 | 90.5 |
| Conversion rate to chlorinated hydrocarbons (%) | 85.0 | 90.8 | 90.9 | 91.2 |
| Conversion rate to CO + CO$_2$ (%) | 1.9 | 2.7 | 8.7 | 2.25 |

The copper powder had a surface area of approximately 300 cm$^2$/g and a mean diameter on the order of 50 μm.

EXAMPLE 2

Test No. 1: Normal operating conditions (not according to the invention) as reference:

Into a 3 m diameter reactor producing 25 tonnes/hour of 1,2-dichloroethane, the operating conditions were as follows:

Temperature: 245 to 250° C.
Pressure: 4 bar
Residence time: 25 to 30 seconds
Catalyst system: 8 tonnes of alumina impregnated with 6% of copper (catalyst) plus silica (22 tonnes). The alumina had a surface area of 357 m$^2$/g, a mean diameter of 53 μ and a pore volume of 33 cm$^3$/100 g and a tap density of 1,192 kg/m$^3$. The silica was a sand from Fontainebleau (pure silica) having a mean diameter of 50 μ and ranging from 20 to 300 μ.

The results obtained are reported in Table II below.

2. Test No. 2: With additions of copper powder:

The procedure of Test No. 1 was repeated, but with additions of copper powder of 50 to 200 kg (this powder had a specific surface area of about 300 cm$^2$/g and a mean diameter of 50 μm). The results obtained are also reported in Table II which follows:

The consumption of catalyst and the consumption of copper powder, expressed in grams per tonne of D 12 produced, are indicated in Table II. The additions of catalyst and copper were made to ensure constant operating conditions.

3. Test No. 3:

The procedure was as in Test No. 2 but, instead of adding catalyst and copper powder, catalyst (the same amount) and very rich catalyst (alumina from Test 1 with a Cu content of 11.5%) were added in an amount such that it represented as much copper as the copper powder in Test 2.

The same results were obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter comprising (i) a catalytically effective amount of an oxychlorination catalyst, (ii) diluent particles of at least one catalytically and chemically inert solid material, and (iii) copper powder or a powdered copper compound.

2. The composition of matter as defined by claim 1, said oxychlorination catalyst comprising alumina particulates impregnated with copper or a copper salt and said diluent particles comprising silica sand.

TABLE II

| | HCl/C$_2$H$_4$ (mol/mol) | O$_2$/C$_2$H$_4$ (mol/mol) | Y$_G$ (%) Conversion rate to HCl | X$_{D12}$ (%) Conversion rate to D12 | R C$_2$H$_4$ (%) Conversion rate to chlorinated products |
|---|---|---|---|---|---|
| Test I | 1.97 | 0.68 | 99.5 | 95.5 | 96.8 |
| Test II | 1.99 | 0.63 | 99 | 96 | 97.3 |

| | VENT GAS (% by volume) | | | | Catalyst consumption (g/t of D12) | Cu % by weight in the bed | Cu consumption (g/t of D12) |
|---|---|---|---|---|---|---|---|
| | C$_2$H$_4$ | CO$_2$ | CO | O$_2$ | | | |
| Test I | 0.42 | 1.20 | 0.60 | 5 | 250 | 1 to 1.2 | 0 |
| Test II | 0.30 | 1.00 | 0.65 | 4.25 | 120 | 2.5 to 3 | 25 |

The catalyst consumption expressed the catalyst additions identical to the catalyst constituting the initial catalytic system (catalyst + silica)
The copper consumption was the consumption of copper powder according to the invention.